US008735091B2

(12) United States Patent
Hyman et al.

(10) Patent No.: US 8,735,091 B2
(45) Date of Patent: May 27, 2014

(54) METHODS FOR INACTIVATION AND EXTRACTION OF ACID-FAST BACTERIA FOR CHARACTERIZATION AND/OR IDENTIFICATION USING MASS SPECTROMETRY

(71) Applicants: Jones M. Hyman, Wake Forest, NC (US); Parampal Deol, Raleigh, NC (US); Elizabeth Miller, Wake Forest, NC (US); Victoria Girard, Lyons (FR); Amber Gates, Durham, NC (US); Sandrine Mailler, Courtenay (FR); Maud Arsac, Saint Chamond (FR); John Walsh, Durham, NC (US)

(72) Inventors: Jones M. Hyman, Wake Forest, NC (US); Parampal Deol, Raleigh, NC (US); Elizabeth Miller, Wake Forest, NC (US); Victoria Girard, Lyons (FR); Amber Gates, Durham, NC (US); Sandrine Mailler, Courtenay (FR); Maud Arsac, Saint Chamond (FR); John Walsh, Durham, NC (US)

(73) Assignee: BioMerieux, Inc., Durham, NC (US)

( * ) Notice: Subject to any disclaimer, the term of this patent is extended or adjusted under 35 U.S.C. 154(b) by 0 days.

(21) Appl. No.: 13/828,119

(22) Filed: Mar. 14, 2013

(65) Prior Publication Data
US 2013/0309714 A1    Nov. 21, 2013

Related U.S. Application Data

(60) Provisional application No. 61/648,420, filed on May 17, 2012.

(51) Int. Cl.
*C12Q 1/24* (2006.01)
(52) U.S. Cl.
USPC .................................... 435/34; 435/253.1
(58) Field of Classification Search
USPC .......................................... 435/34, 253.1
IPC .................................. C12Q 1/24; G01N 1/4077
See application file for complete search history.

(56) References Cited

U.S. PATENT DOCUMENTS

| | | | |
|---|---|---|---|
| 5,948,610 A | 9/1999 | Ho et al. | |
| 6,177,266 B1 | 1/2001 | Krishnamurthy et al. | |
| 6,558,902 B1* | 5/2003 | Hillenkamp | 506/6 |
| 6,833,249 B2* | 12/2004 | Shasany et al. | 435/32 |
| 7,020,559 B1 | 3/2006 | Demirev et al. | |
| 2008/0009029 A1 | 1/2008 | Govorun et al. | |
| 2008/0050829 A1 | 2/2008 | Ivey et al. | |
| 2010/0120085 A1 | 5/2010 | Hyman et al. | |
| 2011/0268744 A1* | 11/2011 | Garthwaite et al. | 424/158.1 |
| 2012/0165246 A1* | 6/2012 | Lindner et al. | 514/2.4 |

FOREIGN PATENT DOCUMENTS

| | | |
|---|---|---|
| WO | WO 2004/014322 | 2/2004 |
| WO | WO 2009/065580 | 5/2009 |

OTHER PUBLICATIONS

Saleeb P. et al. Identification of Mycobacteria in Solid Culture Media by MALDI TOF MS. J of Clinical Microbiology 49(5)1790-4, May 2011.*
Fenselau et al., Characterization of intact microorganisms by MALDI Mass Spectrometry, Mass Spectrometry Reviews, 2001, 157-171, vol. 20, No. 4.
Fox et al., Mass Spectrometry for Species or Strain Identification after Culture or without Culture: Past, Present, and Future, J. Clin. Micro, 2006, 2677-2680, vol. 44, No. 8.
Ingebretsen et al., Rapid identification of clinical mycobacterial strains by matrix-assisted laser desorption ionisation-time-of-flight mass spectrometry (MALDI-TOF MS), 22nd European Congress of Clinical Microbiology and Infection Diseases (ECCMID), dated Mar. 29, 2012.
International Search Report for PCT/US2013/041159 dated Jul. 9, 2013.
Khechine et al., Matrix-Assisted Laser Desorption/Ionization Time-of-Flight Mass Spectrometry Identification of Mycobacteria in Routine Clinical Practice, PLOS One, 2011, e24720, vol. 6, No. 9.
Lanigan et al., Mycobacterial proteome extraction: Comparison of disruption methods, Proteomics, 2004, 1094-1100, vol. 4, No. 4.
Lefmann et al., Novel Mass Spectometry-Based Tool for Genotypic Identification of Mycobacteria, J. Clin. Micro., 2004, 339-346, vol. 42, No. 1.
Ryzhov et al., Rapid Characterization of Spores of *Bacillus cereus* Group Bacteria by Matrix-Assisted Laser Desorption-Ionization Time-of-Flight Mass Sprectrometry, 2000, 3828-3834, vol. 66, No. 9.
Timke et al., Preparation Method for Identification of Mycobacteria by MALDI-TOF Mass Spectrometry, ASM Poster, Mar. 5, 2012.
Co-pending U.S. Appl. No. 13/835,620 'Methods for Inactivation and/or Extraction of a Fungus Test Sample for Characterization and/or Identification Using Mass Spectrometry' filed Mar. 15, 2013.

* cited by examiner

*Primary Examiner* — Ralph Gitomer

(57) ABSTRACT

The present invention is directed to a method for inactivation and/or extraction of acid-fast bacteria (e.g., *mycobacteria* or *nocardia*), the method comprising the following sequential steps: (a) acquiring a test sample known to contain or that may contain acid-fast bacteria and suspending the test sample in a container containing ethanol and beads; (b) bead beating and/or vortexing the container to break up clumps and/or disrupt acid-fast bacteria cells in the container; and (c) subsequently incubating the suspension for at least about 3 minutes at room temperature to inactivate any acid-fast bacteria contained in the test sample. In accordance with the present invention, the test sample can subsequently be pelleted by centrifugation, resuspended with formic acid, acetonitrile added, and subjected to mass spectrometry for characterization and/or identification of the acid-fast bacteria.

28 Claims, 2 Drawing Sheets

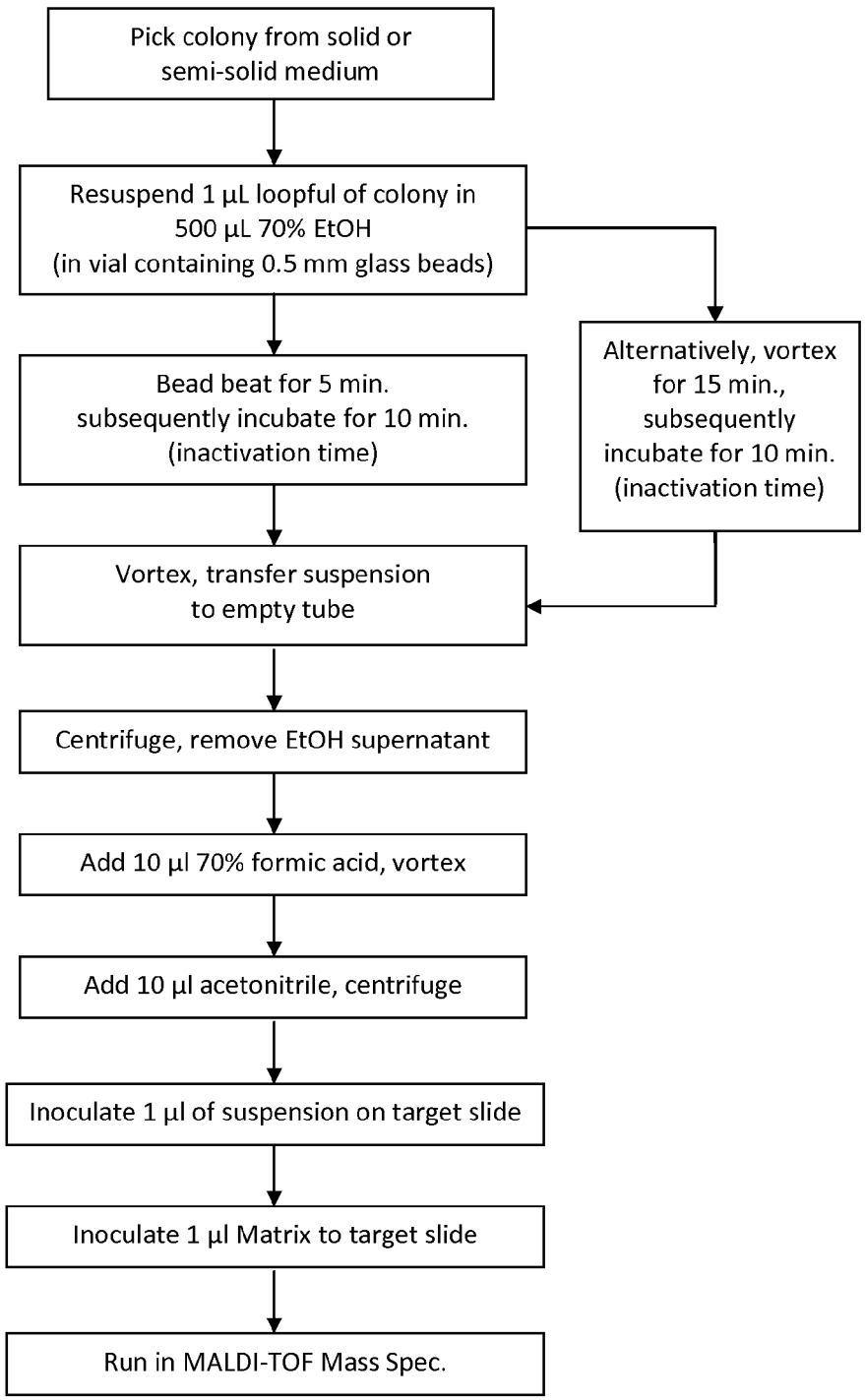
Figure 1. Solid Media Inactivation/Extraction

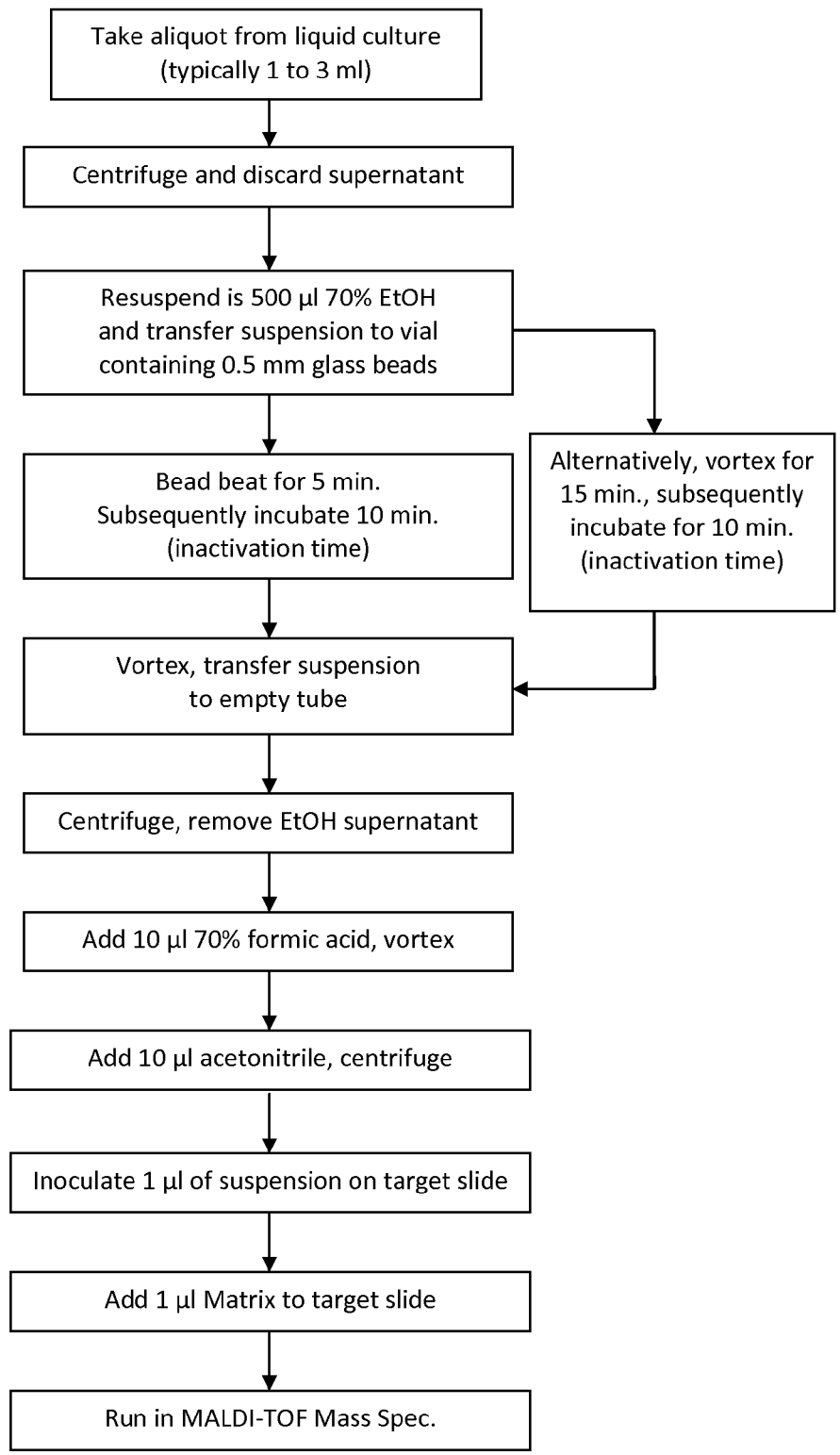
Figure 2. Liquid Media Inactivation/Extraction

METHODS FOR INACTIVATION AND EXTRACTION OF ACID-FAST BACTERIA FOR CHARACTERIZATION AND/OR IDENTIFICATION USING MASS SPECTROMETRY

CROSS REFERENCE TO RELATED APPLICATION

This application claims the benefit of U.S. Provisional Patent Application No. 61/648,420, entitled, "Methods for Inactivation and Extraction of *Mycobacteria* for Characterization and/or Identification using Mass Spectrometry", filed May 17, 2012, which is incorporated herein.

FIELD OF THE INVENTION

The present invention relates to methods for the inactivation and extraction of acid-fast bacteria, such as *Mycobacteria* and *Nocardia*. In particular, the present invention is directed to a method for the rapid characterization and/or identification of *Mycobacteria* or *Nocardia* in a test sample using mass spectrometry.

BACKGROUND OF THE INVENTION

Traditional automated phenotypic ID tests, such as the Vitek®, Phoenix™ and Microscan® systems, or manual phenotypic tests such as API require that microorganisms be in an appropriate growth phase and free of interfering media and blood products in order to provide robust results. These systems use colonies grown from the positive broth for 18-24 hours on plated media. However, in an effort to obtain faster results, some laboratories have reported using these systems with microorganisms isolated from positive blood culture bottles. These direct-from-the-bottle tests are not appropriate for all microorganisms (e.g., Gram-positive cocci), are not validated by the test manufacturers, and generally take 3-8 hours to provide results. Faster and more broadly specific tests are urgently needed in order to provide the physician with clinically relevant results within the first few hours, preferably within an hour after a positive culture result.

Mass spectrometric methods have the potential to allow for identification of microorganisms very quickly, but may encounter interference from the many compounds present in liquid microbiological culture media and in clinical samples such as blood or combinations thereof. The most commonly employed methods for recovering microorganisms directly from positive blood culture broth are two-step differential centrifugation and centrifugation in a serum separator tube.

Other methods for separation, characterization and/or identification of microorganisms have been described, include:

U.S. Pat. No. 6,177,266 discloses a method for the chemotaxonomic classification of bacteria with genus, species and strain specific biomarkers generated by matrix assisted laser desorption ionization time-of-flight mass spectrometry (MALDI-TOF-MS) analysis of either cellular protein extracts or whole cells.

However, there remains a need in the art for efficient and rapid protocols for the inactivation and/or extraction of microorganism test samples for subsequent analysis, characterization and/or identification by mass spectrometry. In particular, inactivation, or cell death, is often necessary for subsequent handling of acid-fast bacteria, such as *Mycobacteria* and *Nocardia*, outside a Biosafety Level-3 (BSL-s/P3) environment.

SUMMARY OF THE INVENTION

In one aspect, the present invention is directed to a method for inactivation and/or extraction of acid-fast bacteria in a test sample, the method comprising the following sequential steps: (a) acquiring a test sample from a solid or semi-solid culture medium known to contain or that may contain acid-fast bacteria (e.g., *mycobacteria* or *nocardia*) and suspending the test sample in a container containing ethanol and beads; (b) bead beating and/or vortexing the container to break up clumps and/or disrupt acid-fast bacteria cells in the container; and (c) subsequently incubating the suspension for at least about 3 minutes to inactivate any acid-fast bacteria contained in the test sample. The acid-fast bacteria (e.g., *mycobacteria* or *nocardia*) sample can be acquired from the solid or semi-solid culture medium using an inoculation loop or a swab.

In one embodiment, the container in step (a) may contain from about 50% to about 100% ethanol, for example, the container may contain about 70% ethanol. The method may further comprise bead beating or vortexing the container in step (b) for about 1 minute to about 30 minutes. In another embodiment, the beads are 0.5 mm glass beads. In one embodiment, the subsequent incubation step (c) comprises an incubated for at least about 3 minutes, or at least about 10 minutes. In another embodiment, the incubation in step (c) is at room temperature.

In another embodiment, the method may further comprise the following additional sequential steps: (d) centrifuging the container to pellet the acid-fast bacteria (e.g., *mycobacteria* or *nocardia*) sample and removing the supernatant; (e) resuspending the acid-fast bacteria pellet in formic acid; and (f) subsequently adding acetonitrile to the container. Optionally, the method further comprises centrifugation of the test sample in the container after step (f). In another optional embodiment, the supernatant from step (d) can be applied directly, or as a water suspension, to a mass spectrometry slide or plate.

The pellet in step (d) may be resuspending using from about 50% to about 90% formic acid, or using about 70% formic acid. After resuspening the pellet, acetonitrile can be added to obtain a final concentration of from about 35% to about 65% acetonitrile, or to obtain a final concentration of about 50%. In one embodiment, the pellet may be resuspended in about 10 µL of formic acid in step (e) and about 10 µL of acetonitrile can be added to the resuspended pellet in step (f).

In accordance with another embodiment, the method further comprises the following additional sequential steps: (g) transferring an aliquot of the supernatant from step (f) to a mass spectrometry target slide and adding a matrix solution to the supernatant; and (h) interrogating the test sample on the slide or plate by mass spectrometry to acquire one or more mass spectra of the acid-fast bacteria (e.g., *mycobacteria* or *nocardia*) and characterizing and/or identifying said acid-fast bacteria in the test sample by comparison of the measured one or more mass spectra with one or more reference mass spectra. Optionally, step (g) comprises transferring an aliquot of the test sample obtained after step (f) to a mass spectrometry slide or plate, allowing the aliquot to dry and subsequently adding a matrix. Any known matrix may be used, for example, the matrix may be alpha-cyano-4-hydroxycinnamic acid (CHCA). In accordance with the present invention, the method can be used for inactivation and/or extraction of *Mycobacteria* or *Nocardia* for subsequent characterization and/or identification. For example, *Mycobacteria* or *Nocar-*

*dia* can be identified to the family, genus, species and/or strain level using mass spectrometry, for example, using MALDI-TOF mass spectrometry.

In another aspect, the present invention is directed to a method comprising the following sequential steps: (a) acquiring a test sample from a liquid culture medium known to contain or that may contain acid-fast bacteria (e.g., *mycobacteria* or *nocardia*) and adding the test sample to a container; (b) centrifuging the container to pellet the acid-fast bacteria in the test sample and subsequently remove the supernatant; (c) resuspending the acid-fast bacteria pellet in ethanol and adding beads to the container; (d) bead beating and/or vortexing the container to break up clumps and/or disrupt acid-fast bacteria cells in the container; and (e) subsequently incubating the suspension for at least about 3 minutes to inactivate any acid-fast bacteria (e.g., *mycobacteria* or *nocardia*) contained in the test sample.

In one embodiment, the acid-fast bacteria (e.g., *mycobacteria* or *nocardia*) pellet can be resuspended in step (c) in from about 50% to about 100% ethanol, for example, the pellet may be resuspended in about 70% ethanol. The method may further comprise bead beating and/or vortexing the container in step (d) for about 1 minute to about 30 minutes. In one embodiment, the beads are 0.5 mm glass beads. In one embodiment, the subsequent incubation step (e) comprises an incubated for at least about 3 minutes, or at least about 10 minutes. In another embodiment, the incubation in step (e) is at room temperature.

In another embodiment, the method may further comprise the following additional sequential steps: (f) centrifuging the container to pellet the inactivated acid-fast bacteria (e.g., *mycobacteria* or *nocardia*) and subsequently remove the supernatant; (g) resuspending the acid-fast bacteria pellet in formic acid; and (h) adding acetonitrile to the container. Optionally, the supernatant from step (f) can be applied directly, or as a water suspension, to a mass spectrometry slide or plate.

The pellet in step (g) may be resuspending using from about 50% to about 90% formic acid, for example, the pellet may be resuspending using 70% formic acid. After resuspending the pellet, acetonitrile can be added to obtain a final concentration of from about 35% to about 65%, for example, to obtain a final concentration of about 50%. In one embodiment, the pellet may be resuspended in 10 µL of formic acid in step (h) and 10 µL of acetonitrile can be added to the resuspended pellet in step (g).

In accordance with this embodiment, the method may further comprises the following additional sequential steps: (i) transferring an aliquot of the supernatant from step (h) to a mass spectrometry target slide and adding a matrix solution; and (j) interrogating the test sample on the slide or plate by mass spectrometry to acquire one or more mass spectra of the acid-fast bacteria and characterizing and/or identifying said acid-fast bacteria in the test sample by comparison of the measured mass spectrum with one or more reference mass spectra. Optionally, step (i) comprises transferring an aliquot (e.g., 1 µL) of the test sample obtained from step (h) to a mass spectrometry slide or plate, allowing the aliquot to dry and subsequently adding a matrix. Any known matrix may be used, for example, the matrix may be alpha-cyano-4-hydroxycinnamic acid (CHCA). In accordance with the present invention, the acid-fast bacteria can be identified to the genus, species and/or strain level using mass spectrometry, for example, MALDI-TOF mass spectrometry.

In still another aspect, the present invention is directed to a method for inactivation and extraction of acid-fast bacteria (e.g., *mycobacteria* or *nocardia*) in a test sample, the method comprising the following sequential steps: (a) acquiring a test sample from a solid or semi-solid culture medium known to contain or that may contain acid-fast bacteria and suspending the test sample in a container containing 70% ethanol and 0.5 mm glass beads; (b) bead beating and/or vortexing the container to break up clumps and/or disrupt acid-fast bacteria cells in the container; (c) subsequently incubating the suspension for at least about 5 minutes at room temperature to inactivate any acid-fast bacteria (e.g., *mycobacteria* or *nocardia*) contained in the test sample; (d) centrifuging the container to pellet the acid-fast bacteria sample and removing the supernatant; (e) resuspending the acid-fast bacteria pellet in at least 3 µL with formic acid; (f) adding at least 3 µL acetonitrile to the container; (g) transferring an aliquot of the supernatant from step (f) to a mass spectrometry target slide and adding a matrix solution to the supernatant; and (h) interrogating the test sample on the slide or plate by mass spectrometry to acquire one or more mass spectra of the acid-fast bacteria and characterizing and/or identifying said acid-fast bacteria in the test sample by comparison of the measured one or more mass spectra with one or more reference mass spectra. In accordance with the present invention, the acid-fast bacteria (e.g., *mycobacteria* or *nocardia*) can be identified to the genus, species and/or strain level, for example, using MALDI-TOF mass spectrometry.

In yet another aspect, the present invention is directed to a method for inactivation and extraction of acid-fast bacteria (e.g., *mycobacteria* or *nocardia*) in a test sample, the method comprising the following sequential steps: (a) acquiring a test sample from a liquid culture medium known to contain or that may contain acid-fast bacteria and adding the test sample to a container, centrifuging the container to pellet the acid-fast bacteria in the test sample and subsequently removing the supernatant; (b) resuspending the acid-fast bacteria pellet in ethanol; (c) subsequently adding 0.5 mm glass beads to the container; (d) bead beating and/or vortexing the container to break up clumps and/or disrupt acid-fast bacteria cells in the container; (e) subsequently incubating the suspension for at least about 5 minutes at room temperature to inactivate any acid-fast bacteria (e.g., *mycobacteria* or *nocardia*) contained in the test sample; (f) centrifuging the container to pellet the inactivated acid-fast bacteria and subsequently remove the supernatant; (g) resuspending the acid-fast bacteria pellet in formic acid; (h) subsequently adding acetonitrile to the container; (i) transferring an aliquot of the supernatant from step (h) to a mass spectrometry target slide and adding a matrix solution to the supernatant; and (j) interrogating the test sample on the slide or plate by mass spectrometry to acquire one or more mass spectra of the acid-fast bacteria and characterizing and/or identifying said acid-fast bacteria in the test sample by comparison of the measured mass spectrum with one or more reference mass spectra. In accordance with the present invention, the acid-fast bacteria (e.g., *mycobacteria* or *nocardia*) can be identified to the genus, species and/or strain level, for example, using MALDI-TOF mass spectrometry.

BRIEF DESCRIPTION OF THE FIGURES

FIG. 1—shows a flow chart of a method for inactivation and extraction of acid-fast bacteria (e.g., *mycobacteria* or *nocardia*) from a solid or semi-solid media, in accordance with one embodiment of the present invention.

FIG. 2—shows a flow chart of a method for inactivation and extraction of acid-fast bacteria (e.g., *mycobacteria* or

*nocardia*) from a liquid media, in accordance with another embodiment of the present invention.

DETAILED DESCRIPTION OF THE INVENTION

The present invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention.

The present assignee's VITEK® MS system (bioMérieux, Inc., St. Louis, Mo.) provides a platform for bacterial identification using a Matrix Assisted Laser Desorption Ionization-Time of Flight (MALDI-TOF) Mass Spectrometer to analyze the protein profile of a sample and match it to a database of known organism profiles. Samples are inoculated onto a target slide, covered with a matrix (e.g., CHCA matrix (α-cyano-4-hydroxy-cinamic acid matrix)), and then processed through the Mass Spectrometer.

Most common clinically-relevant microorganism can be analyzed by inoculating cells directly onto the VITEK® MS target slide. The preparation of acid-fast bacteria (e.g., *mycobacteria* or *nocardia*) samples for analysis differs from the standard procedure in that an inactivation step is necessary in order to make the samples safe for handling outside of a Biosafety Level-3 (BSL-3/P3) environment.

The present applicants have found that incubation in ethanol in conjunction with mechanical disruption provides an effective and rapid method for the inactivation of acid-fast bacteria. Ethanol exposure was shown to be effective when using a process involving a mechanical disruption step followed by subsequent inactivation step by incubating the disrupted sample in ethanol at room temperature for at least 3 minutes, at least 5 minutes or at least 10 minutes. In one embodiment, mechanical disruption is performed using a bead beater (BioSpec, Bartlesville, Okla.), a homogenizer that disrupts cells by agitating a sealed micro centrifuge vial containing sample, extraction solution, and beads (e.g., tiny glass beads). Typically, the beads can be any known beads that can operate to disrupt cells in a container or microcentrifuge tube. For example, the beads can be glass, ceramic, zirconia, silicon, metal, steel, tungsten carbide, garnet, sand, or sapphire beads. In one embodiment, the bead can be from about 0.1 mm to about 1 mm in size, for example, about 0.5 mm in size.

Additional processing steps can then be used to assist in extracting the cellular proteins from the inactivated cells in order to yield clear and consistent spectra. For example, a treatment step in formic acid followed by exposure to acetonitrile can be used to extract and dissolve proteins for subsequent analysis (e.g., by mass spectrometry).

The present invention provides methods for the inactivation, extraction, characterization and/or identification of an unknown acid-fast bacterium in a test sample. The present invention is also directed to a method for the rapid characterization and/or identification of acid-fast bacteria (e.g., *mycobacteria* or *nocardia*) in a test sample using mass spectrometry. The rapid methods allow for characterization and/or identification of acid-fast bacteria more quickly than prior techniques, resulting in faster diagnoses and characterization/identification of test samples. The steps involved in the methods of the invention, from obtaining a sample to characterization/identification of acid-fast bacteria, can be carried out in a very short time frame to obtain clinically relevant actionable information. In certain embodiments, the methods of the invention can be carried out in less than about 120 minutes, e.g., in less than about 110, 100, 90, 80, 70, 60, 50, 40, 30, 20, 15, or 10 minutes. The rapidity of the methods of the invention represents an improvement over prior methods.

In one aspect, the present invention is directed to a method for inactivation of acid-fast bacteria contained or suspected of being contained in a sample or test sample.

In one embodiment of the invention, samples are obtained from a subject (e.g., a patient) having or suspected of having an acid-fast bacterial infection. As used herein, the term "acid-fast bacteria" is intended to encompass any known acid-fast bacteria, including, but not limited to, *Mycobacteria* and *Actinomyces* (including *Nocardia, Rhodococcus, Gordonia, Tsukamurella* and *Dietzia*).

As used herein, the term "*mycobacteria*" or "*Mycobacteria*" is intended to encompass any known *mycobacteria*, including, but not limited to, *Mycobacterium tuberculosis, Mycobacterium bovis, Mycobacterium microti, Mycobacterium africanum, Mycobacterium canetti, Mycobacterium avium, Mycobacterium intracellulare, Mycobacterium scrofulaceum, Mycobacterium kansasii, Mycobacterium malmoense, Mycobacterium xenopi, Mycobacterium marinum, Mycobacterium simiae, Mycobacterium terrae, Mycobacterium ulcerans, Mycobacterium abscessus, Mycobacterium fortuitum, Mycobacterium chelonae,* and *Mycobacterium gordonae.*

As used herein, the term "*nocardia*" or "*Nocardia*" is intended to encompass any known *nocardia*, including, but not limited to, *Nocardia aerocolonigenes, Nocardia africana, Nocardia argentinensis, Nocardia asteroids, Nocardia blackwellii, Nocardia brasiliensis, Nocardia brevicatena, Nocardia camea, Nocardia caviae, Nocardia cerradoensis, Nocardia corallina, Nocardia cyriacigeorgica, Nocardia dassonvillei, Nocardia elegans, Nocardia farcinica, Nocardia nigiitansis, Nocardia nova, Nocardia opaca, Nocardia otitidis-cavarium, Nocardia paucivorans, Nocardia pseudobrasiliensis, Nocardia rubra, Nocardia seriolae, Nocardia transvelencesis, Nocardia uniformis, Nocardia vaccinii,* and *Nocardia veterana.*

As used herein, "characterization" encompasses the broad categorization or classification of biological particles and/or the actual identification of a single genus or species of an acid-fast bacteria. Classification may comprise determination of phenotypic and/or morphologic characteristics for the acid-fast bacteria. For example, characterization of the bacteria may be accomplished based on observable differences, such as, composition, shape, size, pigmentation, clustering and/or metabolism.

As used herein "identification" means determining to which family, genus, species, and/or strain a previously unknown acid-fast bacteria (e.g., *mycobacteria* or *nocarida*) belongs to. For example, identifying a previously unknown acid-fast bacteria to the family, genus, species, and/or strain level.

In one embodiment, the method comprises the following sequential steps: (a) acquiring a test sample from a solid or semi-solid culture medium known to contain or that may contain acid-fast bacteria (e.g., *mycobacteria* or *nocardia*) and suspending the test sample in a container containing ethanol and beads; (b) bead beating and/or vortexing the container to break up clumps and/or disrupt acid-fast bacteria cells in the container; and (c) subsequently incubating the suspension for at least 3 minutes to inactivate any acid-fast bacteria contained in the test sample. Typically, the acid-fast bacteria test sample can be acquired in any known way, for example, the acid-fast bacteria test sample can be acquired, or picked, from the solid or semi-solid culture medium using inoculation loop or a swab.

In one embodiment, the container in step (a) may contain from about 20 µL to about 1 mL of ethanol, or from about 50 µL to about 750 µL, from about 100 µL to about 500 µL, or about 500 µL of ethanol. The ethanol in the container can be from about 50% to about 100% ethanol, from about 60% to about 90% ethanol, or about 50%, 60%, 70%, 80% or 90% ethanol.

As previously described, the acid-fast bacteria test sample can first be subjected to mechanical disruption in step (b), for example, using a bead beater (BioSpec, Bartlesville, Okla.), a homogenizer that disrupts cells by agitating a sealed micro centrifuge vial containing sample, extraction solution, and beads. Typically, the beads can be any known beads that can operate to disrupt cells in a container or microcentrifuge tube. For example, the beads can be glass, ceramic, zirconia, silicon, metal, steel, tungsten carbide, garnet, sand, or sapphire beads. In one embodiment, the bead can be from about 0.1 mm to about 1 mm in size, for example, about 0.5 mm in size. In one embodiment, the beads are 0.5 mm glass beads. Typically, the container is subjected to disruption by beating and/or vortexing the container in step (b) for about 1 minute to about 30 minutes, for about 5 minutes to about 20 minutes, for about 5 minutes to about 10 minutes, or for about 5 minutes or 10 minutes.

After the acid-fast bacteria in the test sample have been disrupted, the container, and thus, the acid-fast bacteria in the test sample, are subjected to inactivation by incubating the container for at least 3 minutes. In one embodiment, the incubation step (c) can be for at least 5 minutes or at least 10 minutes. In another embodiment, the incubation step (c) can be for about 3 minutes to about 30 minutes, for about 5 minutes to about 20 minutes, for about 10 minutes to about 15 minutes, or for about 5, 10, 15, 20 or 30 minutes. In one embodiment, the incubation step (c) is at room temperature.

In another embodiment, the present invention is directed to a method for inactivation of a acid-fast bacteria contained or suspected of being contained in a liquid culture medium.

In one embodiment, the method comprises the following sequential steps: (a) acquiring a test sample from a liquid culture medium known to contain or that may contain acid-fast bacteria (e.g., *mycobacteria* or *nocardia*) and adding the test sample to a container; (b) centrifuging the container to pellet the acid-fast bacteria in the test sample and subsequently removing the supernatant; (c) resuspending the acid-fast bacteria pellet in ethanol and subsequently adding beads to the container; (d) bead beating and/or vortexing the container to break up clumps and/or disrupt acid-fast bacteria cells in the container; and (e) subsequently incubating the suspension for at least 5 minutes to inactivate any acid-fast bacteria (e.g., *mycobacteria* or *nocardia*) contained in the test sample. In one embodiment, the liquid culture sample acquired may be from about 0.5 mL to about 10 mL, from about 1 mL to about 5 mL, from about 1 mL to about 3 mL, or about 1, 2, 3 or 5 mL.

After the centrifugation step (b), the acid-fast bacteria pellet can be resuspended in step (c) in the container with from about 10 µL to about 1 mL of ethanol, or with about 50 µL to about 750 µL, with about 100 µL to about 500 µL, or with about 500 µL. The ethanol used for resuspending the pellet can be from about 50% to about 100% ethanol, from about 60% to about 90% ethanol, or about 50%, 60%, 70%, 80% or 90% ethanol.

As previously described, the acid-fast bacteria test sample can first be subjected to mechanical disruption in step (d), for example, using a bead beater (BioSpec, Bartlesville, Okla.), a homogenizer that disrupts cells by agitating a sealed micro centrifuge vial containing sample, extraction solution, and beads. Typically, the beads can be any known beads that can operate to disrupt cells in a container or microcentrifuge tube. For example, the beads can be glass, ceramic, zirconia, silicon, metal, steel, tungsten carbide, garnet, sand, or sapphire beads. In one embodiment, the bead can be from about 0.1 mm to about 1 mm in size, for example, about 0.5 mm in size. In one embodiment, the beads are 0.5 mm glass beads. Typically, the container is subjected to disruption by beating or vortexing the container in step (d) for about 1 minute to about 30 minutes, for about 5 minutes to about 20 minutes, for about 5 minutes to about 10 minutes, or for about 5 minutes or 10 minutes.

After the acid-fast bacteria in the test sample have been disrupted, the container, and thus, the acid-fast bacteria (e.g., *mycobacteria* or *nocardia*) in the test sample, are subjected to inactivation by incubating the container for at least 3 minutes. In one embodiment, the incubation step (e) can be for at least 5 minutes or for at least 10 minutes. In another embodiment, the incubation step (e) can be for about 5 minutes to about 30 minutes, for about 10 minutes to about 20 minutes, or for about 5, 10, 15, 20 or 30 minutes. In one embodiment, the incubation step (e) is at room temperature.

In another aspect, the present invention is directed to further steps for extraction of a acid-fast bacteria test sample. In one embodiment, the acid-fast bacteria test sample subjected to the extraction steps of the present invention can be the test sample obtained from the previously described methods for inactivation (i.e., the inactivated acid-fast bacteria test samples described above).

The extraction method may comprise the following steps: centrifuging the container to pellet the inactivated acid-fast bacteria (e.g., *mycobacteria* or *nocardia*) and subsequently remove the supernatant; resuspending the acid-fast bacteria pellet in formic acid; and subsequently adding acetonitrile to the container.

For example in one embodiment, the extraction method can be used following the above-described method for inactivation of an acid-fast bacteria (e.g., *mycobacteria* or *nocardia*) test sample acquired from a solid or semi-solid culture media. In accordance with this embodiment, the method may further comprise the following additional sequential steps: (d) centrifuging the container to pellet the acid-fast bacteria sample and removing the supernatant; (e) resuspending the acid-fast bacteria pellet in formic acid; and (f) subsequently adding acetonitrile to the container. Optionally, the method further comprises centrifugation of the test sample in the container after step (f).

In another embodiment, the extraction method can be used following the above-described method for inactivation of a acid-fast bacteria (e.g., *mycobacteria* or *nocardia*) test sample acquired from a liquid culture media. In accordance with this embodiment, the method may further comprise the following additional steps: (f) centrifuging the container to pellet the inactivated acid-fast bacteria and subsequently removing the supernatant; (g) resuspending the acid-fast bacteria pellet in formic acid; and (h) subsequently adding acetonitrile to the container.

In accordance with these embodiment, the pellet may be resuspending using from about 50% to about 100% formic acid, from about 60% to about 90% formic acid, or about 50%, 60%, 70%, 80%, 90% or 100% formic acid. After resuspening the pellet, acetonitrile is added to obtain a final concentration of from about 35% to about 65%, to obtain a final concentration of from about 40% to about 60%, or to obtain a final concentration of about 35%, 40%, 50%, 60%, or 65% acetonitrile. Typically, 100% acetonitrile is used for this step.

In one embodiment, the pellet may be resuspended in at least about 3, 5 or 10 µL of formic acid (in step (e) (from a test sample acquired from a solid or semi-solid medium) or in step (g) (from a liquid test sample)), and at least 3, 5 or 10 µL of acetonitrile can be added to the resuspended pellet. In another embodiment, the pellet may be resuspended using from about 3 µL to about 100 µL of formic acid, about 5 µL to about 80 µL formic acid, about 10 µL to about 50 µL of formic acid, or about 3, 5, 10, 15, 20, 25, 30, 40, 50, 60, 70, 80, 90 or 100 µL, formic acid. In another embodiment, after resuspending the pellet, at least about 3, 5 or 10 µL of acetonitrile are added to the resuspended pellet. For example, from about 3 µL to about 100 µL acetonitrile, from about 5 µL to about 80 µL acetonitrile, 10 µL to about 50 µL acetonitrile, or about 3, 5, 10, 15, 20, 25, 30, 40, 50, 60, 70, 80, 90 or 100 µL acetonitrile, may be added to the resuspended sample.

The present invention also provides methods for characterization and/or identification of an unknown acid-fast bacteria (e.g., *mycobacteria* or *nocardia*) using mass spectrometry, e.g., using matrix assisted laser desorption ionization time-of-flight (MALDI-TOF mass spectrometry). In accordance with the present invention, the characterization and/or identification steps may follow the inactivation and extraction steps described above.

In accordance with this embodiment, the methods may further comprise the following additional sequential steps: transferring an aliquot of the supernatant from step (f) (e.g., for sample preparation from a solid or semi-solid media), of from step (h) (e.g., for sample preparation from a liquid culture media), to a mass spectrometry target slide and adding a matrix solution to the supernatant; and interrogating the test sample on the slide or plate by mass spectrometry to acquire one or more mass spectra of the acid-fast bacteria and characterizing and/or identifying said acid-fast bacteria in the test sample by comparison of the measured one or more mass spectra with one or more reference mass spectra. Optionally, the transferred aliquot can be from about 0.5 µL to about 2.5 µL, or about 1 µL. As is well known in the art, the aliquot is typically allowed to dry and subsequently a matrix solution is added. In general, any known matrix in the art can be used. For example, in one embodiment, the matrix is alpha-cyano-4-hydroxycinnamic acid (CHCA). In accordance with the present invention, the acid-fast bacteria (e.g., *mycobacteria* or *nocardia*) can be identified to the family, genus, species and/or strain level using, for example, MALDI-TOF mass spectrometry, as described further hereinbelow.

After the mass spectrometry plate or slide has been prepared the slide or plate is inserted into the mass spectrometer. After the time required to pump the sample down (i.e. remove atmospheric gases from the sample so that it is in an environment of 10–5 to 10–7 torr), the sample is introduced into the ionization chamber of the mass spectrometer. The sample is aligned with the system. When optimal alignment is achieved, the nitrogen laser is pulsed. The absorption of the laser energy by the matrix causes it to ablate from the plate's surface due to the high energy deposited. As a side effect, portions of the acid-fast bacteria cells are also vaporized and ionized in the process. These ions are accelerated to a known kinetic energy by the generation of an electrostatic field between the plate and the entrance to the mass spectrometer's flight tube (i.e. this portion of the system is the mass/charge discriminator). All singly charged ions, regardless of mass, will have the same kinetic energy at the entrance to the flight tube, but they will have velocities that are inversely proportional to their masses. From there, ions move down the flight tube towards the detector, and lighter ions will arrive before heavier ions (the flight tube is the mass/charge discriminator). The detector generates an electrical charge every time an ion impacts the detector. The output of the detector is digitized and the output displays mass/charge ratio on one axis and number of impacts on the other axis. In one embodiments, the acid-fast bacteria on the slide or plate can be interrogated using any known mass spectrometry techniques, such as MALDI-TOF mass spectrometry, desorption electrospray ionization (DESI) mass spectrometry, GC mass spectrometry, LC mass spectrometry, electrospray ionization (ESI) mass spectrometry and Selected Ion Flow Tube (SIFT) spectrometry, or other known mass spectrometry technique.

According to the invention, control measurements are taken for known acid-fast bacteria, thus allowing for correlation of measured test data with characterization of the acid-fast bacteria of interest using various mathematical methods known to those skilled in the art. For example, the data from samples may be compared with the baseline or control measurements utilizing software systems known to one skilled in the art. More particularly, the data may be analyzed by a number of multivariate analysis methods, such as, for example, General Discriminant Analysis (GDA), Partial Least Squares Discriminant Analysis (PLSDA), Partial Least Squares regression, Principal Component Analysis (PCA), Parallel Factor Analysis (PARAFAC), Neural Network Analysis (NNA) and/or Support Vector Machine (SVM). These methods may be used to classify unknown acid-fast bacteria (e.g., *mycobacteria* or *nocardia*) of interest into relevant groups based on existing nomenclature, and/or into naturally occurring groups based on the organism's metabolism, pathogenicity and/or virulence in designing the system for monitoring, detecting and/or characterizing the organism as described previously. In one embodiment, after acquisition of a one or more mass spectra for acid-fast bacteria, the one or more mass spectra can be input into the "Saramis" microorganism identification software (bioMérieux, Inc., St. Louis, Mo.) for analysis, and thus, for characterization and/or identification of the acid-fast bacteria.

In yet another embodiment, non-spectroscopic measurements from the detection system, such as detection times and growth rates can be used to assist in the characterization and/or identification of acid-fast bacteria from test sample.

In some embodiments of the invention, characterization and/or identification of the acid-fast bacteria in the test sample need not involve identification of an exact species. Characterization may encompass the broad categorization or classification of biological particles as well as the actual identification of a single species. As used herein "identification" means determining to which family, genus, species, and/or strain a previously unknown acid-fast bacteria belongs to. For example, identifying a previously unknown acid-fast bacteria to the family, genus, species, and/or strain level.

In still another aspect, as shown in FIG. 1, the present invention is also directed to a method for inactivation and extraction of acid-fast bacteria (e.g., *mycobacteria* or *nocardia*) in a test sample, the method comprising the following steps: (a) acquiring a test sample from a solid or semi-solid culture medium known to contain or that may contain acid-fast bacteria and suspending the test sample in a container containing 70% ethanol and 0.5 mm glass beads; (b) bead beating and/or vortexing the container for at least 5 minutes to break up clumps and/or disrupt acid-fast bacteria cells in the container; (c) subsequently incubating the suspension for at least 10 minutes at room temperature to inactivate any acid-fast bacteria contained in the test sample; (d) centrifuging the container to pellet the acid-fast bacteria and removing the supernatant; (e) resuspending the acid-fast bacteria pellet in 10 µL with formic acid; (f) adding 10 µL acetonitrile to the container; (g) transferring a 1 µL aliquot of the supernatant from step (f) to a mass spectrometry target slide and adding 1 µL matrix solution to the supernatant; and (h) interrogating the test sample on the slide or plate by mass spectrometry to acquire one or more mass spectra of the acid-fast bacteria and characterizing and/or identifying said acid-fast bacteria by comparison of the measured one or more mass spectra with reference mass spectra. In accordance with the present invention, the acid-fast bacteria (e.g., *mycobacteria* or *nocardia*) can be identified to the family, genus, species and/or strain level.

In yet another aspect, as shown in FIG. 2, the present invention is also directed to a method for inactivation and extraction of acid-fast bacteria in a test sample, the method comprising the following steps: (a) acquiring a 2 mL test sample from a liquid culture medium known to contain or that may contain acid-fast bacteria and adding the test sample to a container, centrifuging the container to pellet the acid-fast bacteria in the test sample and subsequently remove the supernatant; (b) resuspending the acid-fast bacteria pellet in 500 µL of 70% ethanol; (c) subsequently adding 0.5 mm glass beads to the container; (d) bead beating the container for at least 5 minutes to break up clumps and/or disrupt acid-fast bacteria cells in the container; (e) subsequently incubating the suspension for at least 10 minutes at room temperature to inactivate any acid-fast bacteria contained in the test sample; (f) centrifuging the container to pellet the inactivated acid-fast bacteria and subsequently remove the supernatant; (g) resuspending the acid-fast bacteria pellet in 10 µL formic acid; (h) subsequently adding 10 µL acetonitrile to the container; (i) transferring a 1 µL aliquot of the supernatant from step (h) to a mass spectrometry target slide and adding a 1 µL of matrix solution to the supernatant; and (j) interrogating the test sample on the slide or plate by mass spectrometry to acquire one or more mass spectra of the acid-fast bacteria and characterizing and/or identifying said acid-fast bacteria by comparison of the measured one or more mass spectra with reference mass spectra. In accordance with the present invention, the acid-fast bacteria can be identified to the family, genus, species and/or strain level.

That which is claimed is:

1. A method for inactivation and extraction of acid-fast bacteria in a test sample, the method comprising the following sequential steps:
   (a) acquiring a test sample from a solid or semi-solid culture medium containing acid-fast bacteria and suspending the test sample in a container containing ethanol and beads;
   (b) bead beating the container to break up clumps and/or disrupt the acid-fast bacteria cells in the container; and
   (c) subsequently inactivating the acid-fast bacteria cells contained in the test sample by incubating the suspension for at least about 5 minutes at room temperature;
   (d) centrifuging the container to pellet the acid-fast bacteria sample and removing supernatant;
   (e) resuspending the acid-fast bacteria pellet in formic acid; and
   (f) subsequently extracting cellular proteins from the inactivated cells by adding acetonitrile to the container, wherein the formic acid and acetonitrile extract and dissolve cellular proteins from the inactivated cells.

2. The method of claim 1, wherein the method further comprises the following additional sequential steps:
   (g) centrifuging the container to pellet the inactivated acid-fast bacteria from step (f) and subsequently transferring an aliquot of supernatant to a mass spectrometry target slide and adding a matrix solution to supernatant; and
   (h) interrogating the test sample on the mass spectrometry target slide by mass spectrometry to acquire one or more mass spectra of the acid-fast bacteria and characterizing and/or identifying said acid-fast bacteria in the test sample by comparison of the one or more mass spectra with one or more reference mass spectra.

3. The method of claim 1, wherein said acid-fast bacteria is *Mycobacteria* or *Nocardia*.

4. The method of claim 1, wherein supernatant from step (d) is applied directly, or as a water suspension, to a mass spectrometry slide or plate.

5. The method as claimed in claim 1, wherein said container contains 70% ethanol.

6. The method as claimed in claim 1, wherein said beads are 0.5 mm glass beads.

7. The method as claimed in claim 1, wherein the acid-fast bacteria pellet is resuspended in 70% formic acid in step (e).

8. The method as claimed in claim 1, wherein acetonitrile is added to a final concentration of from about 35% to about 65%.

9. The method of claim 1, wherein the method further comprises bead beating or vortexing the container in step (b) for about 1 minute to about 30 minutes.

10. The method of claim 1, wherein the method further comprises incubating the suspension in step (c) for at least about 5 minutes.

11. The method of claim 1, wherein the method further comprises incubating the suspension in step (c) for at least about 10 minutes.

12. The method of claim 1, wherein the pellet is resuspended in at least about 3 µL of formic acid in step (e).

13. The method of claim 1, wherein at least about 3 µL of acetonitrile is added to the resuspended pellet in step (f).

14. The method as claimed in claim 2, wherein step (g) comprises transferring an aliquot of the test sample to a mass spectrometry slide or plate, allowing the aliquot to dry and subsequently adding a matrix.

15. The method as claimed in claim 2, wherein said matrix solution added in step (g) is alpha-cyano-4-hydroxycinnamic acid (CHCA).

16. The method as claimed in claim 2, wherein said acid-fast bacteria is identified to the genus, species and/or strain level.

17. A method for inactivation and extraction of acid-fast bacteria from a solid or semi-solid culture medium, and subsequently characterizing and/or identifying said acid-fast bacteria, the method comprising the following sequential steps:
   (a) acquiring a test sample from a solid or semi-solid culture medium containing acid-fast bacteria and suspending the test sample in a container containing 70% ethanol and 0.5 mm glass beads;
   (b) bead beating the container to break up clumps and/or disrupt acid-fast bacteria cells in the container;
   (c) subsequently inactivating the acid-fast bacteria cells contained in the test sample by incubating the suspension for at least about 5 minutes at room temperature;
   (d) centrifuging the container to pellet the acid-fast bacteria and removing supernatant;

(e) resuspending the acid-fast bacteria pellet in at least 3 µL with formic acid;

(f) extracting cellular proteins from the inactivated cells by adding at least 3 µL acetonitrile to the container, wherein the formic acid and acetonitrile extract and dissolve cellular proteins from the inactivated cells;

(g) centrifuging the container to pellet the inactivated acid-fast bacteria from step (f) and subsequently transferring an aliquot of supernatant to a mass spectrometry target slide and adding a matrix solution to supernatant; and (h) interrogating the test sample on the mass spectrometry target slide by mass spectrometry to acquire one or more mass spectra of the acid-fast bacteria and characterizing and/or identifying said acid-fast bacteria by comparison of the one or more mass spectra with one or more reference mass spectra.

18. The method of claim 17, wherein said acid-fast bacteria is *Mycobacteria* or *Nocardia*.

19. The method of claim 17, wherein said acid-fast bacteria is identified to the family, genus, species and/or strain level.

20. A method for inactivation and extraction of acid-fast bacteria in a test sample, the method comprising the following sequential steps:

(a) acquiring a test sample from a liquid culture medium containing acid-fast bacteria and adding the test sample to a container, centrifuging the container to pellet the acid-fast bacteria in the test sample and subsequently removing supernatant;

(b) resuspending the acid-fast bacteria pellet in ethanol;

(c) adding glass beads to the container;

(d) bead beating the container to break up clumps and/or disrupt acid-fast bacteria cells in the container;

(e) subsequently inactivating the acid-fast bacteria cells contained in the test sample by incubating the suspension for at least about 5 minutes at room temperature;

(f) centrifuging the container to pellet the inactivated acid-fast bacteria and subsequently remove supernatant;

(g) resuspending the acid-fast bacteria pellet in formic acid; and (h) subsequently extracting cellular proteins from the inactivated cells by adding acetonitrile to the container, wherein the formic acid and acetonitrile extract and dissolve cellular proteins from the inactivated cells;

(i) centrifuging the container to pellet the inactivated acid-fast bacteria from step (h) and subsequently transferring an aliquot of supernatant to a mass spectrometry target slide and adding a matrix solution to supernatant; and (j) interrogating the test sample on the mass spectrometry target slide by mass spectrometry to acquire one or more mass spectra of the acid-fast bacteria and characterizing and/or identifying said acid-fast bacteria in the test sample by comparison of the one or more mass spectra with one or more reference mass spectra.

21. The method of claim 20, wherein said acid-fast bacteria is *Mycobacteria* or *Nocardia*.

22. The method as claimed in claim 20, wherein said container contains 70% ethanol.

23. The method as claimed in claim 20, wherein said beads are 0.5 mm glass beads.

24. The method as claimed in claim 20, wherein the pellet in step (d) is resuspending in 70% formic acid.

25. The method as claimed in claim 20, wherein said acetonitrile is added in step (h) to a final concentration of from about 35% to about 65%.

26. The method of claim 20, wherein the method further comprises bead beating or vortexing the container in step (b) for about 1 minute to about 30 minutes.

27. The method of claim 1, wherein the method further comprises incubating the suspension in step (c) for at least about 10 minutes.

28. The method of claim 20, wherein said acid-fast bacteria sample is identified to the family, genus, species and/or strain level.

* * * * *